US00PP27706P3

(12) United States Plant Patent
Morgan et al.

(10) Patent No.: US PP27,706 P3
(45) Date of Patent: Feb. 21, 2017

(54) ***GENTIANA* PLANT NAMED 'RI0405128'**

(50) Latin Name: *Gentiana scabra×triflora*
Varietal Denomination: RI0405128

(71) Applicant: RHINDO INTERNATIONAL LIMITED, Mt. Albert, Auckland (NZ)

(72) Inventors: Edmond R. Morgan, Auckland (NZ); Takashi Hikage, Hachimantai (JP)

(73) Assignee: Rhindo International Limited, Auckland (NZ)

( * ) Notice: Subject to any disclaimer, the term of this patent is extended or adjusted under 35 U.S.C. 154(b) by 76 days.

(21) Appl. No.: 14/545,711

(22) Filed: Jun. 9, 2015

(65) Prior Publication Data

US 2015/0366121 P1 Dec. 17, 2015

Related U.S. Application Data

(60) Provisional application No. 61/997,855, filed on Jun. 11, 2014.

(51) Int. Cl.
*A01H 5/02* (2006.01)

(52) U.S. Cl.
USPC ..... Plt./433

(58) Field of Classification Search
USPC ..... Plt./433
See application file for complete search history.

*Primary Examiner* — Anne Grunberg
(74) *Attorney, Agent, or Firm* — Lathrop & Gage LLP

(57) ABSTRACT

A new and distinct *Gentiana scabra×triflora* variety named 'RI0405128' is described. The variety results from selection among a population of seedlings derived from controlled crossing of the *Gentiana* varieties known as 'SR3004' (not patented) and '13-414' (not patented). The new variety is distinguished from others by its purple flower color and compact plant form.

2 Drawing Sheets

Genus and species: *Gentiana scabra×triflora.*

BACKGROUND OF THE INVENTION

Seedlings obtained from the deliberate crossing of the *Gentiana scabra×triflora* selections 'SR3004' (female parent) (not patented) and '13-414' (male parent) (not patented), in 2005, were planted out at Palmerston North, New Zealand, where the cross was also conducted. In 2008, 'RI0405128' was asexually propagated and underwent simultaneous evaluation at Palmerston North and in Hachimantai City, Japan. In 2010, 'RI0405128' was selected for its purple flower color and branching habit in both trial planting locations, New Zealand and Japan. Plants have been asexually propagated by both cuttings and tissue culture and subsequently found to be true to type demonstrating that the characteristics of the new variety 'RI0405128', are stable and transmitted without change through succeeding generations.

SUMMARY OF THE INVENTION

The new cultivar 'RI0405128' was selected for its unique combination of characteristics including the deep purple flower color, flowers borne on strong, upright stems, and a plant habit that is compact and uniform. The multiple branching habit and short stature of the plant indicate conformation suitable for culture as a potted plant.

'RI0405128' is distinguished from a number of other varieties by the following characteristics:

'RI0405128' has purple flowers whereas the flowers of the *Gentiana* hybrid 'True Blue' (U.S. Plant Pat. No. 20,433) are blue.

'RI0405128' has purple flowers whereas the flowers of *Gentiana scabra* are blue, pink, or white.

'RI0405128' has purple flowers whereas the purple color does not appear in the flowers of *Gentiana makinoi.*

'RI0405128' has short stems and purple flowers whereas its parent, 'SR3004' has long stems and red flowers.

'RI0405128' has short stems and purple flowers whereas its parent, '13-414' has long stems and pink flowers.

BRIEF DESCRIPTION OF THE PHOTOGRAPHS

Figure 1:
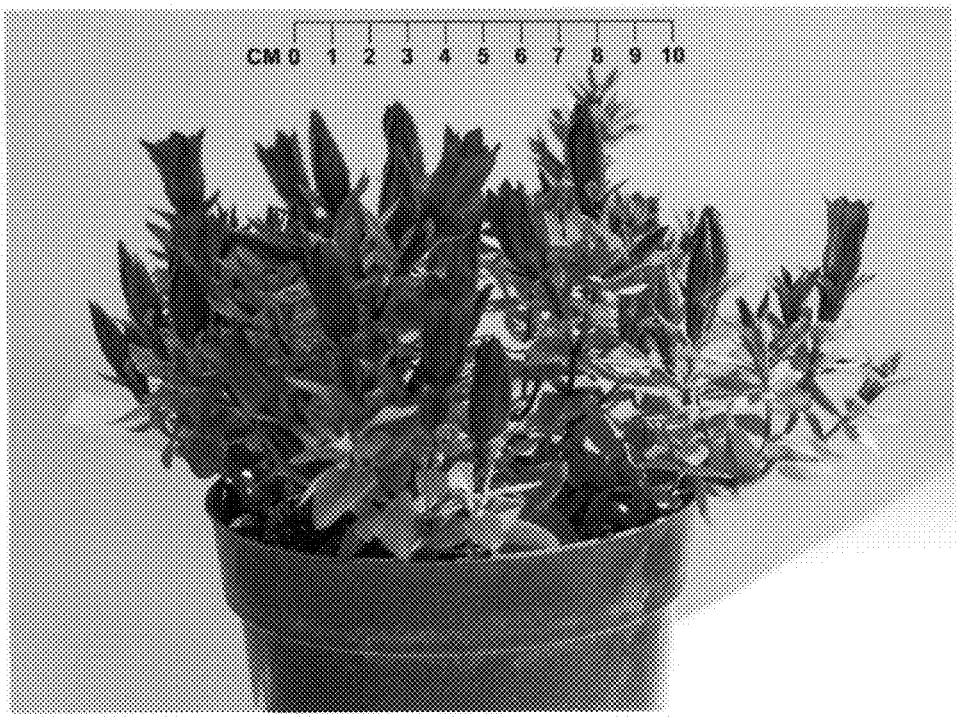

FIG. 1: 'RI0405128' plant showing branching habit and short stature suitable for culture as a potted plant.

Figure 2:
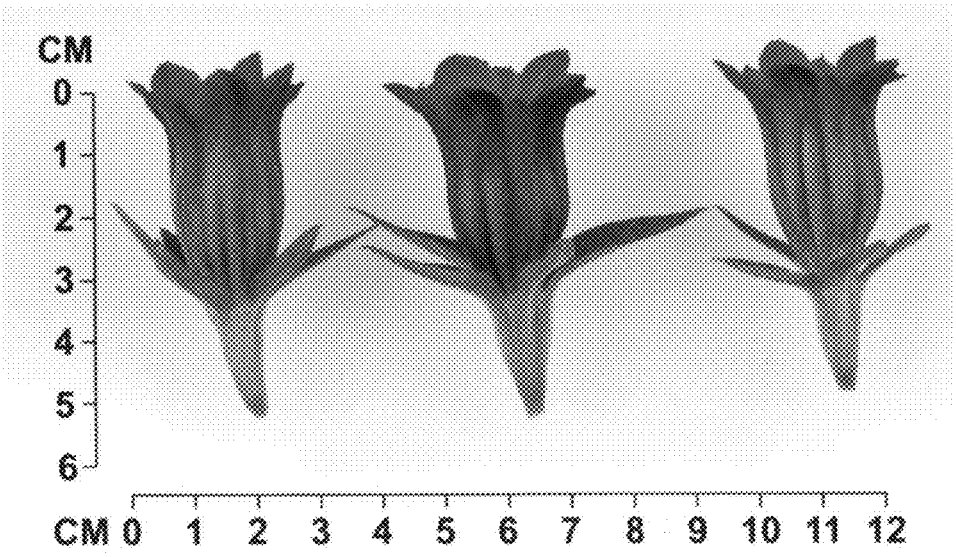

FIG. 2: flowers of 'RI0405128' in studio.

Figure 3:
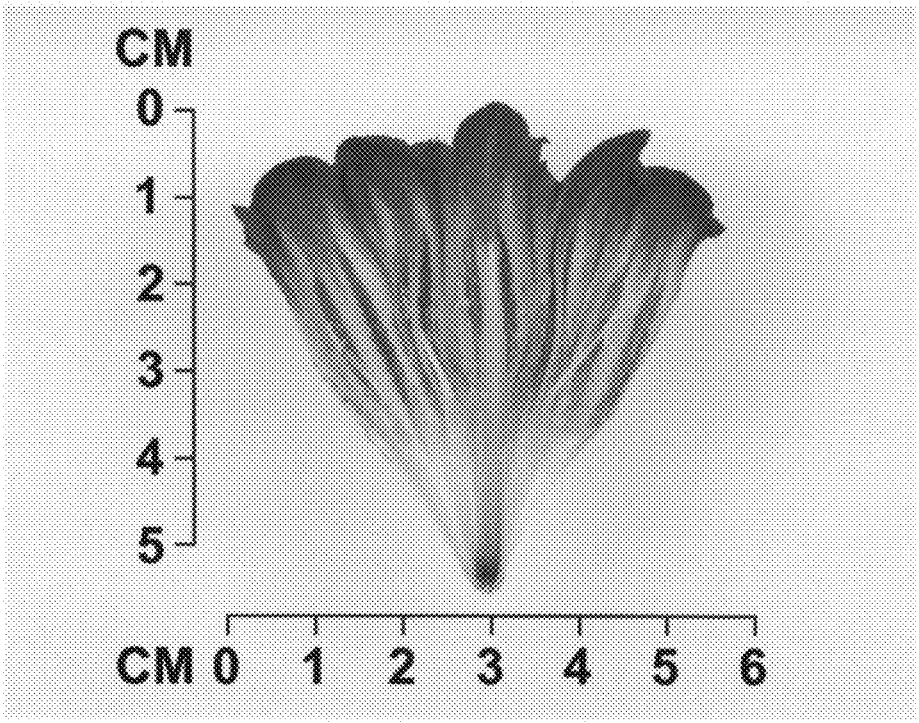

FIG. 3: longitudinal section of 'RI0405128' flower.

DETAILED DESCRIPTION

The following is a description of the new variety with color terminology in accordance with The Royal Horticultural Society Colour Charts (R.H.S.C.C.) Fourth edition (2001). The plants were grown at Palmerston North, New Zealand. The observations were made during 2015 in New Zealand on 13-month old plants planted in 15 cm diameter pots grown outdoors in a well sheltered area with 80 mm pot spacing.

Plant: The plant is herbaceous perennial with a semi-erect growth habit and medium vigour. Its average height was 15 cm and spread 42 cm.

Stem: The main flowering stem length was on average 100 mm with an average thickness of 1.3 mm. The stem shape in cross section at the mid point was circular. Color of the stem observed when the plant was actively growing was near purple group N77A. Side shoots were present. The average length of internodes in the central third of the stem was 9.8 mm and the average number of internodes on the side shoots was 3. The position of the longest leaf was in the central third of the stem.

Leaves: The leaf arrangement was opposite and decussate. The average leaf length was 24 mm and the average width at the widest point 12 mm. Leaf shape was ovate and in cross section the leaf folded upwards. In longitudinal section the leaf shape was concave. The leaf tip shape was acute with the leaf margin entire. There was no leaf twisting present. The average number of leaf conspicuous veins was 3. The color of the upper surface of the leaf was near green 143A and the under-side was near green 143D. Pubescence on the under and upper surface of the leaf was absent.

Flower: Flowers were terminal and auxiliary in position and found in alternate open clusters along the stem and did not have a fragrance. The average number of flowers per cluster was 4.6 flowers. The mean date of 50% open flowers at Palmerston North, New Zealand, was 12 February. Under low light intensity the degree of flowers closing was strong. The flower was campanulate in shape, with the ovary superior, five petals fused to form corolla with lobes at top. Stamens were attached near base of the corolla tube. The average pedicel length was 19 mm and the average peduncle length was 122 mm. The average length of the flower was 44 mm and style length average was 4.2 mm.

Corolla: The corolla average length was 52 mm, average aperture diameter was 13.6 mm and the average diameter of the corolla tube at the widest point was 14 mm. The surface of the corolla was smooth and the color of the corolla stripe, mid petal was near purple group N77A and the lobe was near purple-violet N81 A. The lobes were ovate in shape with the lobe average length 13 mm and width 11 mm. There were approximately 5 lobes per corolla. A paracorolla was present.

Calyx: The shape of the calyx tube was funnel-shaped, and calyx lobe was narrow lanceolate. The average length of the calyx tube was 17 mm with an average tube diameter of 7 mm and the average calyx diameter from tip of lobe to tip of opposite lobe was 31 mm. The color was near green group 143C with near purple N79A shadowing.

Anther: The anther was fully developed, and cylindrical in shape.

Ease of propagation: Propagates readily from tissue culture or stem cuttings.

The invention claimed is:

1. A new and distinct *Gentiana* plant named 'RI0405128', substantially as illustrated and described herein.

* * * * *